(12) United States Patent
Howard et al.

(10) Patent No.: US 12,148,523 B2
(45) Date of Patent: Nov. 19, 2024

(54) ELECTRONIC INTERFACE FOR HEALTHCARE RESOURCE SCHEDULING

(71) Applicant: Teambuilder LLC, Newtown, CT (US)

(72) Inventors: David Howard, Newtown, CT (US); Michael Paraskakis, New York, NY (US)

(73) Assignee: TEAMBUILDER LLC, Newtown, CT (US)

( * ) Notice: Subject to any disclaimer, the term of this patent is extended or adjusted under 35 U.S.C. 154(b) by 0 days.

(21) Appl. No.: 18/097,086

(22) Filed: Jan. 13, 2023

(65) Prior Publication Data
US 2024/0105317 A1  Mar. 28, 2024

Related U.S. Application Data

(63) Continuation of application No. 17/950,355, filed on Sep. 22, 2022.

(51) Int. Cl.
G16H 40/20 (2018.01)
G06Q 10/0631 (2023.01)
G16H 40/63 (2018.01)

(52) U.S. Cl.
CPC ....... *G16H 40/20* (2018.01); *G06Q 10/06315* (2013.01); *G16H 40/63* (2018.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS 5,911,134 A    6/1999  Castonguay
8,788,308 B1 * 7/2014  Cox .................. G06Q 10/0631
                                                    705/7.17
(Continued)

FOREIGN PATENT DOCUMENTS

WO    2000077665 A8    11/2001

OTHER PUBLICATIONS

Raunak et al. 2013, "Resource Management for Complex, Dynamic Environments," in IEEE Transactions on Software Engineering, vol. 39, No. 3, pp. 384-402, Mar. 2013, doi: 10.1109/TSE.2012.31.*

(Continued)

*Primary Examiner* — Robert W Morgan
*Assistant Examiner* — Charles P Coleman
(74) *Attorney, Agent, or Firm* — Moore & Van Allen PLLC

(57) ABSTRACT

A system for healthcare resource scheduling is configured to calculate differential demand for a type of healthcare resource; based on the differential demand for the type of healthcare resource, determine, via an optimization engine, a suggested resource assignment; cause an operator device to display a user interface that displays a visual representation of the differential demand for the type of healthcare resource and a visual representation of the suggested resource assignment, wherein the visual representation of the suggested resource assignment is selectable by an operator of the operator device; receive, from the operator device, an operator selection comprising a selection of the suggested resource assignment in the user interface; and transmit an assignment notification to a computing device associated with a particular available resource of the type of healthcare resource.

20 Claims, 6 Drawing Sheets

(58) Field of Classification Search
CPC ........ G16H 20/13; G16H 20/17; G16H 30/00;
G16H 40/00; G16H 50/00; G16H 70/00;
G16H 80/00; G16H 40/20; G16H 40/63;
G06Q 50/22–24; G06Q 10/06315
USPC .................................................. 705/2, 3, 20
See application file for complete search history.

(56) References Cited

U.S. PATENT DOCUMENTS

| | | | |
|---|---|---|---|
| 11,010,699 B1* | 5/2021 | Lu | G06F 3/04842 |
| 11,062,802 B1 | 7/2021 | McNair | |
| 2001/0051888 A1 | 12/2001 | Mayhak | |
| 2004/0039628 A1 | 2/2004 | Thompson | |
| 2004/0117046 A1 | 6/2004 | Colle | |
| 2006/0047553 A1 | 3/2006 | Fuhrmann | |
| 2006/0177041 A1 | 8/2006 | Warner | |
| 2010/0198609 A1 | 8/2010 | Mellin | |
| 2013/0080202 A1 | 3/2013 | Cameron | |
| 2016/0063196 A1* | 3/2016 | Dube | G16H 40/20 |
| | | | 705/2 |
| 2017/0024523 A1 | 1/2017 | Gutfraind | |
| 2017/0039338 A1* | 2/2017 | Khindaria | G16H 70/20 |
| 2017/0098181 A1 | 4/2017 | Herman | |
| 2017/0177806 A1* | 6/2017 | Fabian | G16Z 99/00 |
| 2018/0324186 A1* | 11/2018 | Dintenfass | G06F 21/31 |
| 2018/0349821 A1* | 12/2018 | Zhang | G06Q 10/0633 |
| 2019/0304595 A1* | 10/2019 | Bergman | G06N 3/04 |
| 2020/0334602 A1* | 10/2020 | Anderson | G06Q 10/1053 |
| 2020/0411169 A1 | 12/2020 | Brown | |
| 2020/0411170 A1* | 12/2020 | Brown | G06N 20/00 |
| 2021/0192426 A1 | 6/2021 | Yu | |
| 2022/0020476 A1 | 1/2022 | Souissi | |
| 2022/0092519 A1 | 3/2022 | Hunter | |
| 2022/0115124 A1* | 4/2022 | Gutman | G16H 50/20 |
| 2022/0147907 A1 | 5/2022 | Venkatesh | |
| 2022/0270021 A1* | 8/2022 | Glocker | G06Q 10/063112 |
| 2023/0004921 A1* | 1/2023 | Padalalu | G06Q 10/063116 |
| 2023/0316203 A1* | 10/2023 | Luijckx | G06Q 10/06375 |
| | | | 705/7.37 |
| 2023/0359961 A1* | 11/2023 | Chobe | G06F 16/90335 |

OTHER PUBLICATIONS

Naeem et al. 2015, "Wireless Resource Allocation in Next Generation Healthcare Facilities," in IEEE Sensors Journal, vol. 15, No. 3, pp. 1463-1474, Mar. 2015, doi: 10.1109/JSEN.2014.2363571.*

* cited by examiner

ELECTRONIC INTERFACE FOR HEALTHCARE RESOURCE SCHEDULING

CROSS-REFERENCE TO RELATED APPLICATION

This application is a continuation of co-pending patent application Ser. No. 17/950,355, filed Sep. 22, 2022, and titled "Electronic Interface For Healthcare Resource Scheduling", which is hereby incorporated herein by reference in its entirety.

FIELD OF THE INVENTION

The present invention embraces a system and electronic interface for healthcare resource scheduling.

BACKGROUND

In healthcare settings, demand for healthcare resources fluctuates over time, making it difficult to create an efficient schedule for said resources.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

In some embodiments, the present invention embraces a system for healthcare resource scheduling, the system comprising: at least one non-transitory storage device; and at least one processing device coupled to the at least one non-transitory storage device, wherein the at least one processing device is configured to: establish a communication channel with a data source; receive a data transmission from the data source, where the data transmission comprises data regarding scheduled availability of a type of healthcare resource; receive a second data transmission from the data source, where the second data transmission comprises data associated with demand for the type of healthcare resource; based on the data regarding scheduled availability of a type of healthcare resource and the data associated with demand for the type of healthcare resource, calculate differential demand for the type of healthcare resource; based on the differential demand for the type of healthcare resource, determine, via an optimization engine, a suggested resource assignment; cause an operator device to display a user interface that displays a visual representation of the differential demand for the type of healthcare resource and a visual representation of the suggested resource assignment, where the visual representation of the suggested resource assignment is selectable by an operator of the operator device; receive, from the operator device, an operator selection comprising a selection of the suggested resource assignment in the user interface; and transmit an assignment notification to a computing device associated with a particular available resource of the type of healthcare resource.

In some embodiments, the system is configured for, in response to the operator selection comprising the selection of the suggested resource assignment, causing the operator device to display, via the user interface, a selectable list of available resources of the type of healthcare resource, the selectable list of available resources comprising the particular available resource of the type of healthcare resources; and receiving a second operator selection, the second operator selection comprising a selection of the particular available resource from the selectable list of available resources; where the assignment notification is transmitted to the computing device associated with the particular available resource in response to the second operator selection.

In some embodiments, the data regarding scheduled availability of the type of healthcare resource comprises information identifying a resource, resource type, and resource location.

In some embodiments, the system is configured for, in response to the operator selection, querying the data regarding scheduled availability of the type of healthcare resource; and determining the selectable list of available resources, where the selectable list of available resources is ranked based on at least one predetermined characteristic.

In some embodiments, the type of healthcare resource comprises a category of personnel utilized by a healthcare provider.

In some embodiments, the suggested resource assignment comprises a suggested shift for a category of personnel utilized by a healthcare provider.

In some embodiments, the data source is an external data source.

In some embodiments, calculating differential demand for the type of healthcare resource further comprises calculating, for each time period of a plurality of time periods, a demand for the type of healthcare resource.

In some embodiments, the visual representation of the differential demand for the type of healthcare resource comprises a visual representation of the demand for the type of healthcare resource for each time period of the plurality of time periods.

In some embodiments, the differential demand is calculated, at least in part, based on historical availability data for the type of healthcare resource.

In some embodiments, the differential demand is calculated, at least in part, based on historical demand data for the type of healthcare resource.

In some embodiments, the optimization engine is configured to determine the suggested resource assignment based on an optimization algorithm and at least one predetermined parameter.

In some embodiments, the system is configured for receiving an assignment acceptance from the computing device associated with the particular available resource.

In some embodiments, the system is configured for receiving an assignment denial from the computing device associated with the particular available resource; and transmitting the assignment notification to a second computing device associated with a second available resource based on a third operator selection comprising a selection of the second available resource from the selectable list of available resources.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
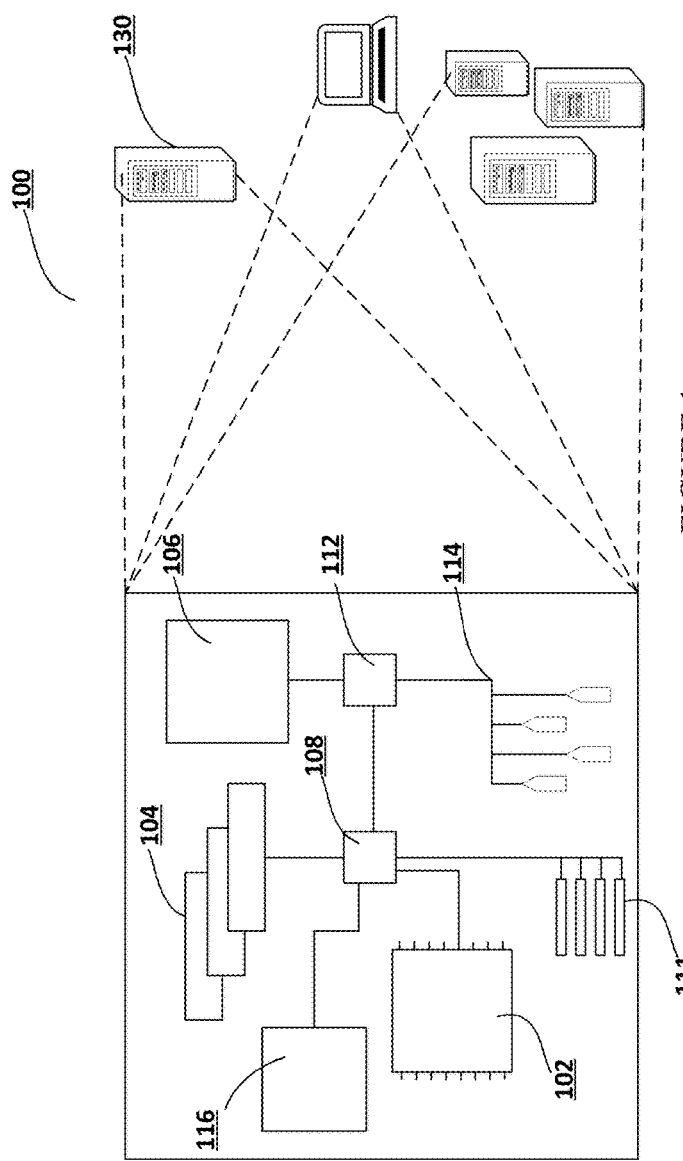
Figure 1:
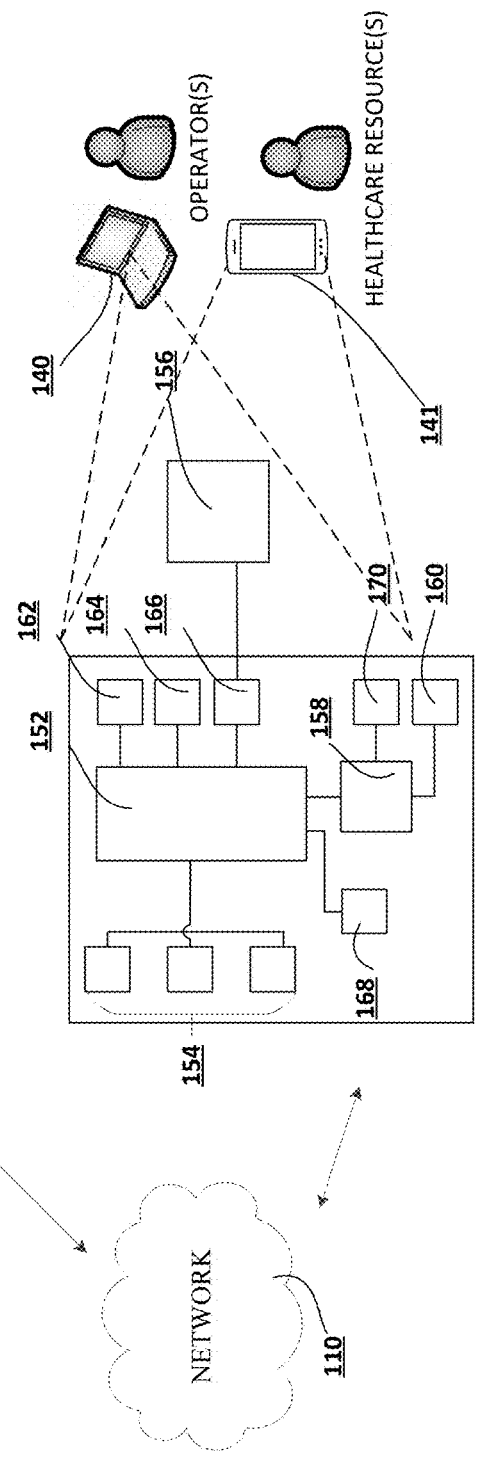
Figure 2:
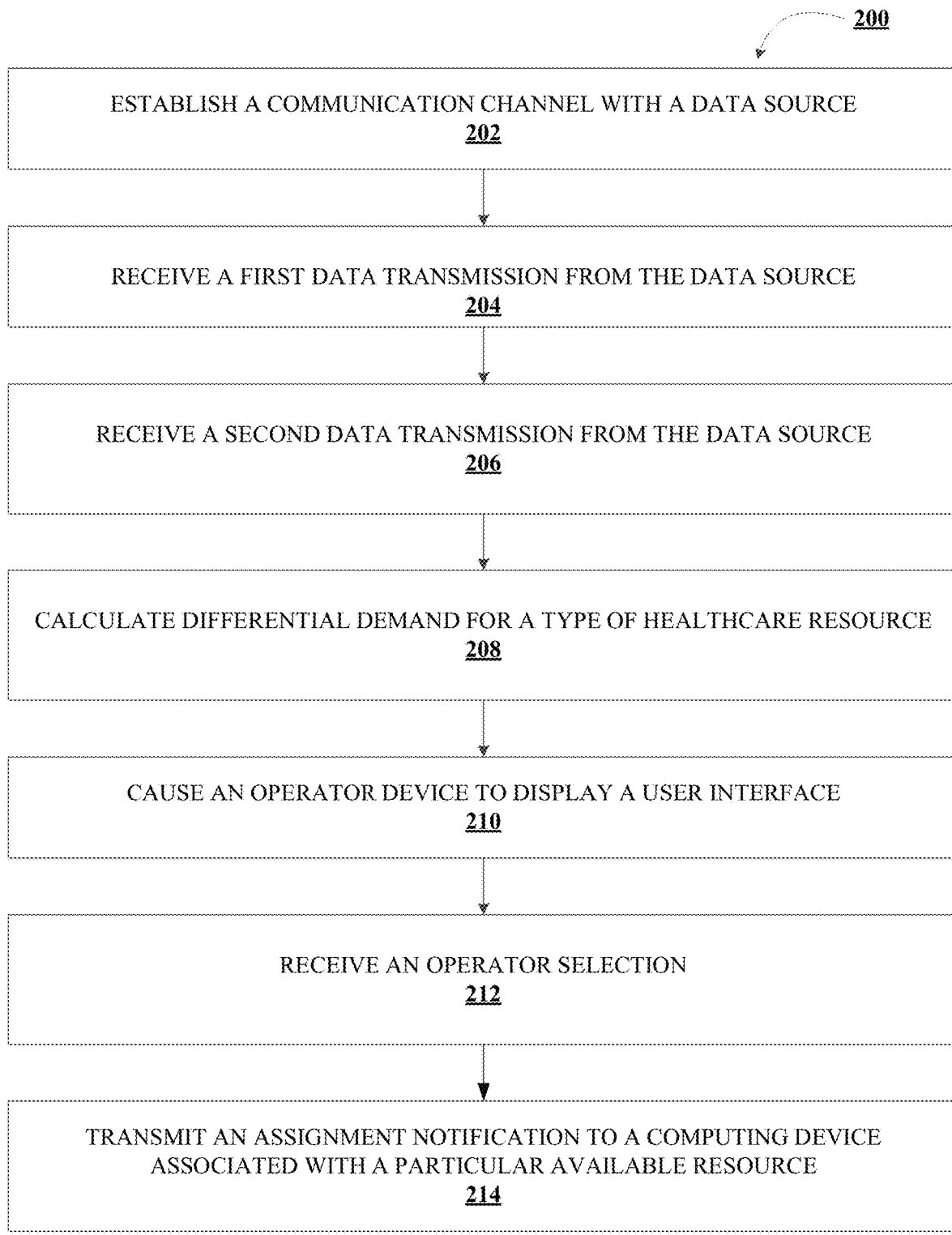
Figure 3:
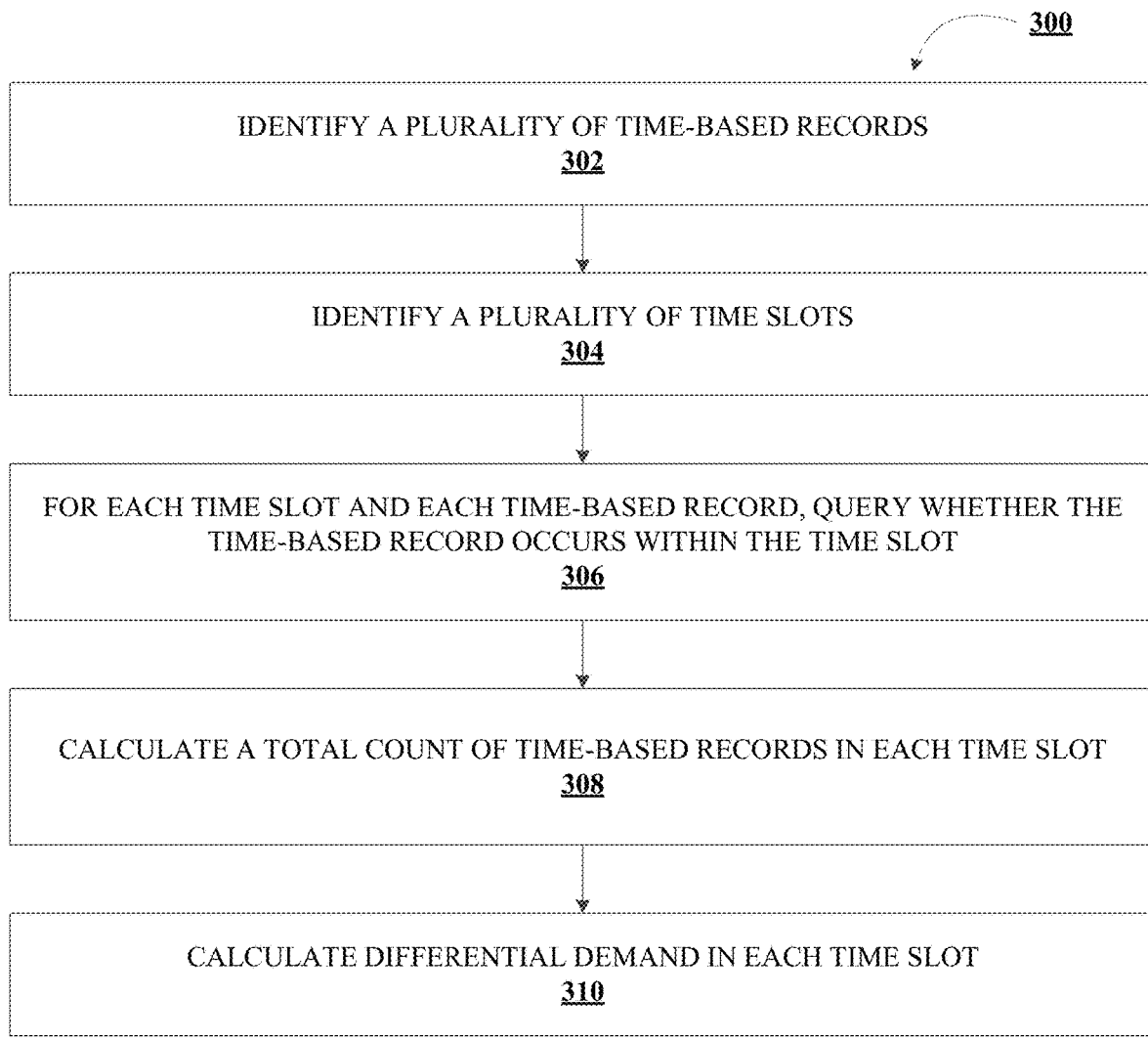
Figure 4:
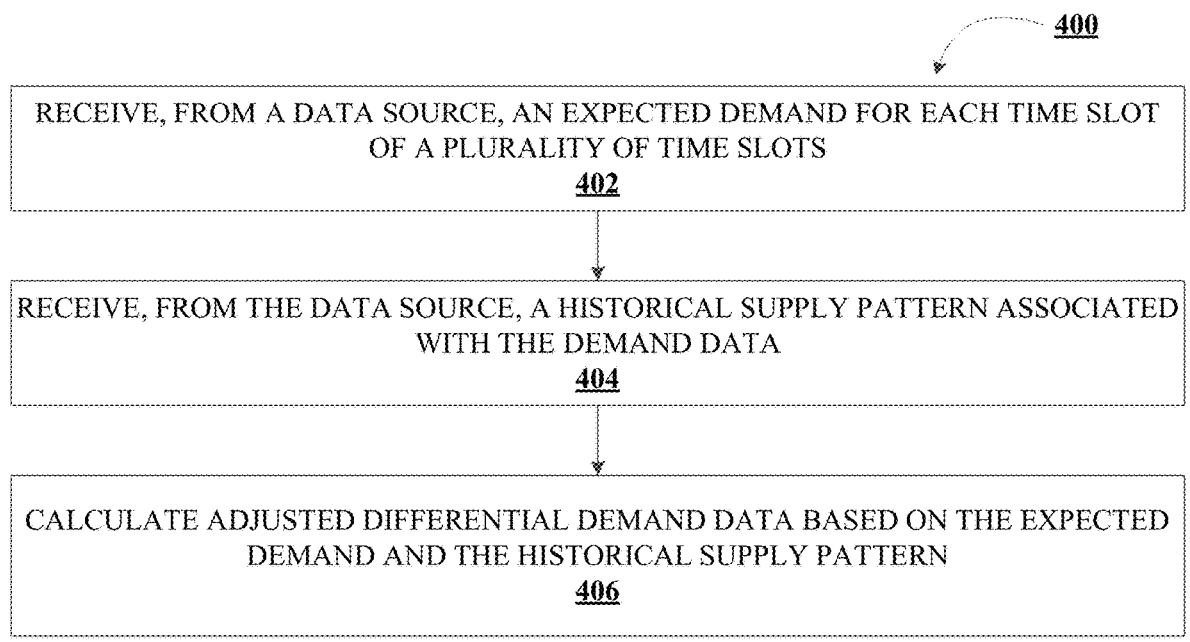
Figure 5:
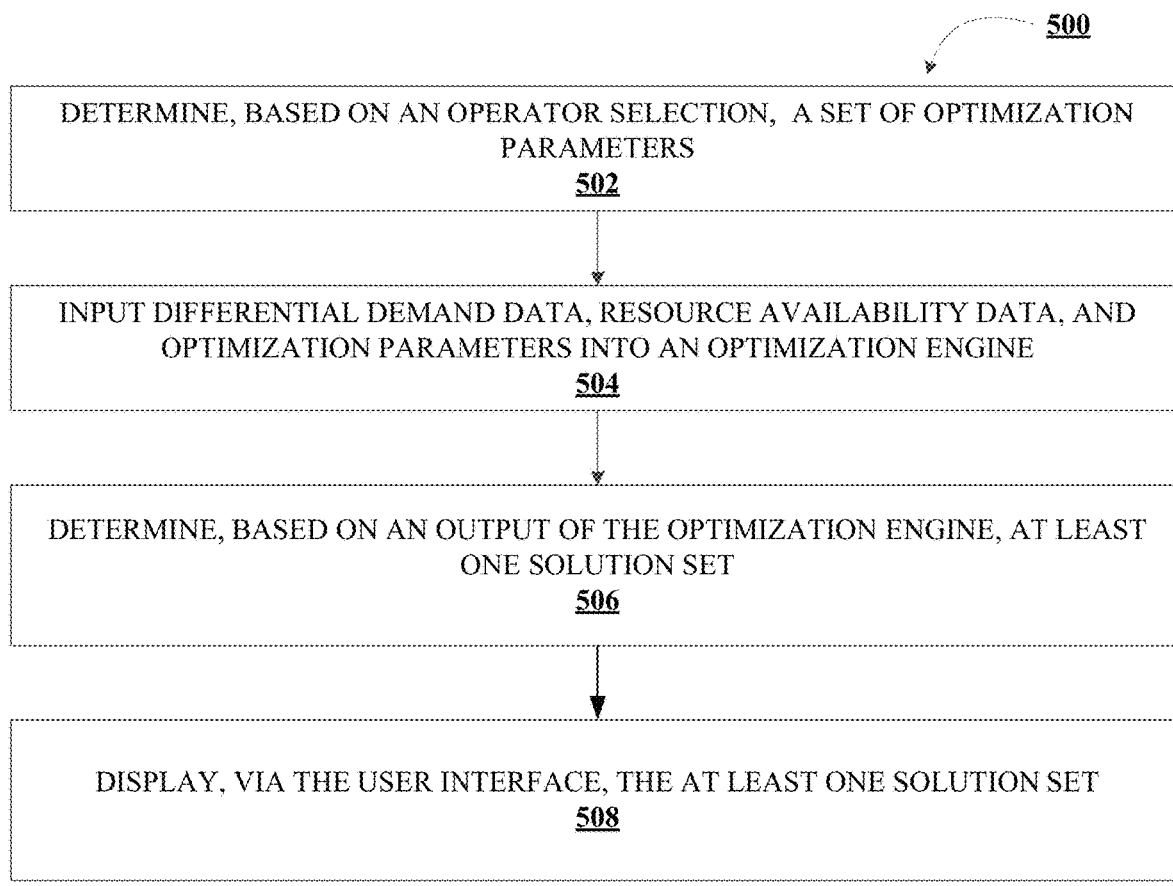
Figure 6:
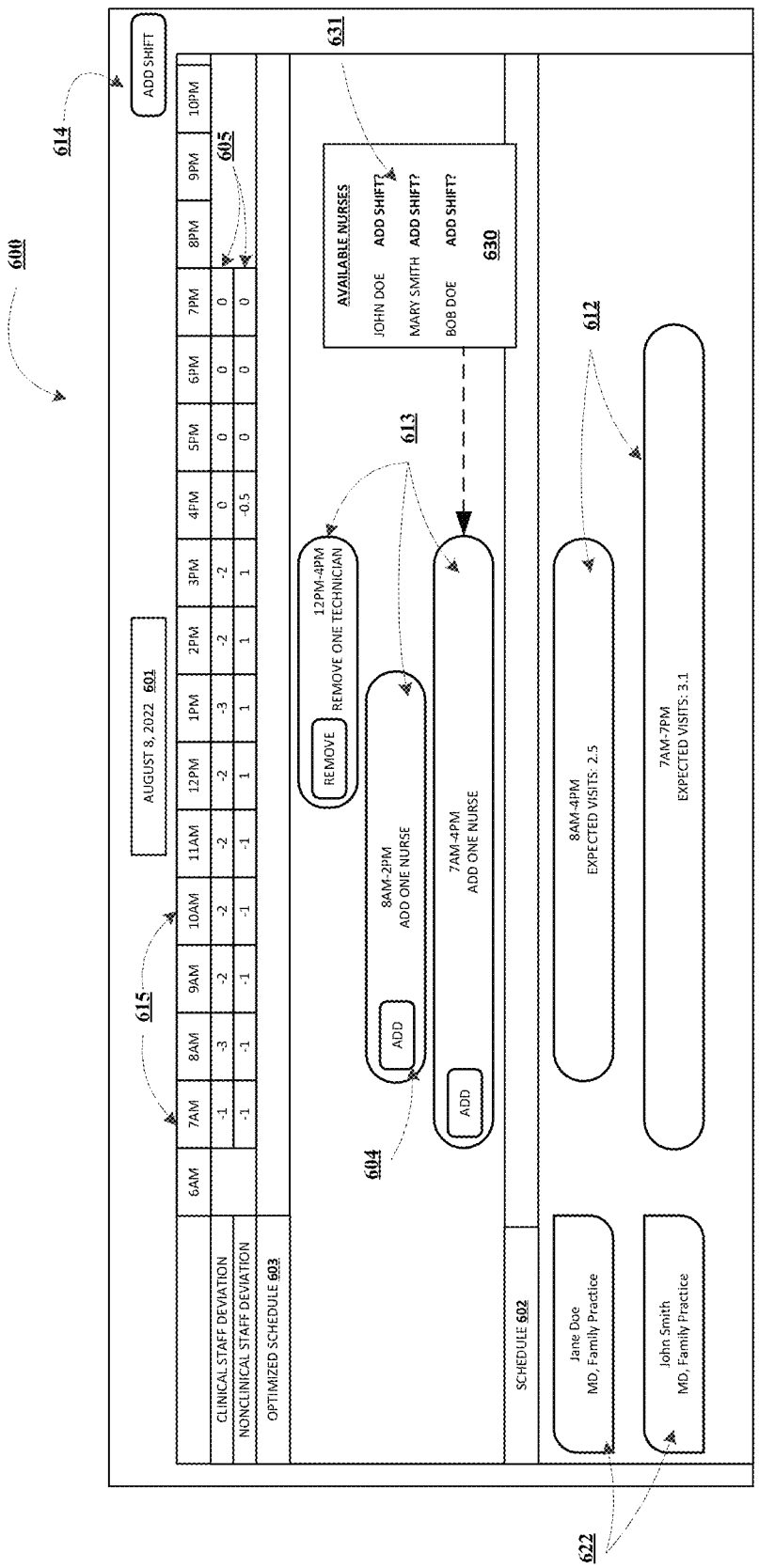

Having thus described embodiments of the invention in general terms, reference will now be made to the accompanying drawings, wherein:

FIG. 1 illustrates an operating environment for the healthcare resource scheduling system, in accordance with one embodiment of the present disclosure;

FIG. 2 is a flow diagram illustrating a process using the healthcare resource scheduling system, in accordance with one embodiment of the present disclosure;

FIG. 3 is a flow diagram illustrating a process using the healthcare resource scheduling system, in accordance with one embodiment of the present disclosure;

FIG. 4 is a flow diagram illustrating a process using the healthcare resource scheduling system, in accordance with another embodiment of the present disclosure;

FIG. 5 is a flow diagram illustrating a process using the healthcare resource scheduling system, in accordance with another embodiment of the present disclosure; and FIG. 6 is a block diagram illustrating a user interface for the healthcare resource scheduling system, in accordance with an embodiment of the present disclosure.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

"Entity" or "managing entity" as used herein may refer to any organization, entity, or the like which employs healthcare resources and/or utilizes technology infrastructure configured for managing healthcare resources via one or more computing systems. The computing systems may comprise applications relating to one or more operations of the entity. As such, the entity or managing entity may be any institution, group, association, establishment, authority, or the like, utilizing information technology resources for managing healthcare resources. For example, the entity or managing entity may comprise a hospital, clinic, healthcare facility, university, and/or the like.

"Entity system" or "managing entity system" as used herein may refer to the computing systems, devices, software, applications, communications hardware, and/or other resources used by the entity to perform the functions as described herein. Accordingly, the entity system may comprise desktop computers, laptop computers, servers, Internet-of-Things ("IoT") devices, networked terminals, mobile smartphones, smart devices (e.g., smart watches), network connections, and/or other types of computing systems or devices and/or peripherals along with their associated applications. "Application" as used herein may refer to any computer or software program which may serve one or more purposes relating to the entity, such as execution of products or services, data analysis and management, information security, internal and/or external communications, and/or any other function performed by the entity.

"Operator" as used herein may refer to an individual or entity associated with an entity or managing entity. In some instances, an "operator" is an individual or group who has a relationship with the managing entity, such as an employee, administrator, or the like. Accordingly, as used herein the term "operator device" or "user device" may refer to laptops, mobile phones, personal computing devices, tablet computers, wearable devices, and/or any portable electronic device capable of receiving and/or storing data therein and are owned, operated, or managed by a managing entity.

"Healthcare resource" as used herein may refer to an individual that performs work for with the entity or managing entity. In some instances, a "healthcare resource" is an employee or contractor with the managing entity and may work for the managing entity based on a schedule. For example, a "healthcare resource" may be a technician, doctor, nurse, clinical staff member, non-clinical staff member, nurse practitioner, specialist, and/or the like. A "resource type" as used herein may refer to a specific resource category or job title, such as clinical staff, technician, nurse, and/or the like. An individual healthcare resource may be associated with multiple resource types, such as "pharmacist," "clinical staff," and "full-time staff."

As used herein, an "engine" may refer to core elements of a computer program, or part of a computer program that serves as a foundation for a larger piece of software and drives the functionality of the software. An engine may be self-contained, but externally-controllable code that encapsulates powerful logic designed to perform or execute a specific type of function. In one aspect, an engine may be underlying source code that establishes file hierarchy, input and output methods, and how a specific part of a computer program interacts or communicates with other software and/or hardware. The specific components of an engine may vary based on the needs of the specific computer program as part of the larger piece of software. In some embodiments, an engine may be configured to retrieve resources created in other computer programs, which may then be ported into the engine for use during specific operational aspects of the engine. An engine may be configurable to be implemented within any general purpose computing system. In doing so, the engine may be configured to execute source code embedded therein to control specific features of the general purpose computing system to execute specific computing operations, thereby transforming the general purpose system into a specific purpose computing system.

It should also be understood that "operatively coupled," as used herein, means that the components may be formed integrally with each other, or may be formed separately and coupled together. Furthermore, "operatively coupled" means that the components may be formed directly to each other, or to teach other with one or more components located between the components that are operatively coupled together. Furthermore, "operatively coupled" may mean that the components are detachable from each other, or that they are permanently coupled together. Furthermore, "operatively coupled" may mean that components may be electronically connected.

In healthcare settings, demand for healthcare resources fluctuates over time, making it difficult to create an efficient schedule for said resources. As such, there is a need for an improved resource scheduling interface that automatically responds to changes in resource demand. The present invention addresses this need by providing a user interface whereby an operator such as a hospital administrator, shift supervisor, ambulatory director, practice manager, ambulatory team lead, and/or the like is presented with differential staffing demand over time as well as suggestions for additional shifts and available employees to fill said shifts. In addition, the system is configured to communicate with an employee's computing device, allowing for real-time transmission of shift requests based on selections via the user interface. Furthermore, the system is configured to dynamically calculate differential staffing demand by employing future demand predictions based on historical data. As such, the system facilitates increased staffing efficiency over time.

The invention described herein can provide several technological improvements. For example, the system described herein can automatically create suggested shifts for available healthcare resources as demand data and availability data update in real-time. The system may also provide an improved interface for presenting suggested shifts to a user, receiving a user selection of a suggested shift, and then automatically scheduling or communicating with the selected resource. Furthermore, the system described herein can be used continuously at a scale that cannot be handled using manual techniques, such as manual scheduling. For example, predictive modeling may be used to adjust actual demand data, allowing the system to build schedules in real-time based on predicted demand data. In contrast, manual scheduling would require manually building a new schedule every time demand data was updated, resulting in a far greater use of time and computational resources. The present invention also solves a technical problem that arises only within the realm of computer networks, such as providing an improved user interface and establishing communication channels with external data sources to compile and analyze disparate data.

FIG. 1 presents an exemplary block diagram of the operating environment 100 for a healthcare resource scheduling system 130, in accordance with an embodiment of the invention. FIG. 1 provides a unique system that includes specialized servers and system communicably linked across a distributive network of nodes required to perform the functions of the process flows described herein in accordance with embodiments of the present invention.

As illustrated, the operating environment 100 includes a network 110, the system 130, an operator input system 140, and a resource input system 141. Also shown in FIG. 1 is one or more operators(s) of the operator input system 140 and one or more healthcare resource(s) of the resource input system 141. The operator input system 140 is intended to represent various forms of mobile devices, such as laptops, personal digital assistants, reality (XR) devices, and/or the like, and non-mobile devices such as desktops, video recorders, audio/video player, radio, workstations, and/or the like. The operator may be a person who uses the operator input system 140 to execute one or more processes described herein using one or more applications stored thereon. The one or more applications may be configured to communicate with the system 130 and/or resource input system 141, execute a process or method, input information onto a user interface presented on the operator input system 140, or the like. The applications stored on the user input system 140 and the system 130 may incorporate one or more parts of any process flow described herein.

As shown in FIG. 1, the system 130, the operator input system 141, and the resource input system 141 are each operatively and selectively connected to the network 110, which may include one or more separate networks. In addition, the network 110 may include a telecommunication network, local area network (LAN), a wide area network (WAN), and/or a global area network (GAN), such as the Internet. It will also be understood that the network 110 may be secure and/or unsecure and may also include wireless and/or wired and/or optical interconnection technology.

The system 130 is intended to represent various forms of digital computers, such as laptops, desktops, workstations, electronic kiosk devices, blade servers, mainframes, or any combination of the aforementioned. The operator input system 140 and resource input system 141 are intended to represent various forms of personal devices, such as laptops, desktops, mobile devices, smartphones, and other similar computing devices. The components shown here, their connections and relationships, and their functions, are meant to be exemplary only, and are not meant to limit implementations of the inventions described and/or claimed in this document.

In accordance with some embodiments, the system 130 may include a processor 102, memory 104, a storage device 106, a high-speed interface 108 connecting to memory 104, and a low-speed interface 112 connecting to low speed bus 114 and storage device 106. Each of the components 102, 104, 106, 108, 111, and 112 are interconnected using various buses, and may be mounted on a common motherboard or in other manners as appropriate. The processor 102 can process instructions for execution within the system 130, including instructions stored in the memory 104 or on the storage device 106 to display graphical information for a GUI on an external input/output device, such as display 116 coupled to a high-speed interface 108. In other implementations, multiple processors and/or multiple buses may be used, as appropriate, along with multiple memories and types of memory. Also, multiple systems, same or similar to system 130 may be connected, with each system providing portions of the operations (e.g., as a server bank, a group of blade servers, or a multi-processor system). In some embodiments, the system 130 may be a server managed by an entity. The system 130 may be located at a facility associated with the entity or remotely from the facility associated with the entity.

The memory 104 stores information within the system 130. In one implementation, the memory 104 is a volatile memory unit or units, such as volatile random access memory (RAM) having a cache area for the temporary storage of information. In another implementation, the memory 104 is a non-volatile memory unit or units. The memory 104 may also be another form of computer-readable medium, such as a magnetic or optical disk, which may be embedded and/or may be removable. The non-volatile memory may additionally or alternatively include an EEPROM, flash memory, and/or the like. The memory 104 may store any one or more of pieces of information and data used by the system in which it resides to implement the functions of that system. In this regard, the system may dynamically utilize the volatile memory over the non-volatile memory by storing multiple pieces of information in the volatile memory, thereby reducing the load on the system and increasing the processing speed.

The storage device 106 is capable of providing mass storage for the system 130. In one aspect, the storage device 106 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier may be a non-transitory computer- or machine-readable storage medium, such as the memory 104, the storage device 104, or memory on processor 102.

In some embodiments, the system 130 may be configured to access, via the 110, a number of other computing devices (not shown). In this regard, the system 130 may be configured to access one or more storage devices and/or one or more memory devices associated with each of the other computing devices. In this way, the system 130 may implement dynamic allocation and de-allocation of local memory resources among multiple computing devices in a parallel or distributed system. Given a group of computing devices and a collection of interconnected local memory devices, the fragmentation of memory resources is rendered irrelevant by configuring the system 130 to dynamically allocate memory based on availability of memory either locally, or in any of the other computing devices accessible via the network. In effect, it appears as though the memory is being allocated from a central pool of memory, even though the space is distributed throughout the system. This method of dynamically allocating memory provides increased flexibility when the data size changes during the lifetime of an application and allows memory reuse for better utilization of the memory resources when the data sizes are large.

The high-speed interface 108 manages bandwidth-intensive operations for the system 130, while the low speed controller 112 manages lower bandwidth-intensive operations. Such allocation of functions is exemplary only. In some embodiments, the high-speed interface 108 is coupled to memory 104, display 116 (e.g., through a graphics processor or accelerator), and to high-speed expansion ports 111, which may accept various expansion cards (not shown). In such an implementation, low-speed controller 112 is coupled to storage device 106 and low-speed expansion port 114. The low-speed expansion port 114, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The system 130 may be implemented in a number of different forms, as shown in FIG. 1. For example, it may be implemented as a standard server, or multiple times in a group of such servers. Additionally, the system 130 may also be implemented as part of a rack server system or a personal computer such as a laptop computer. Alternatively, components from system 130 may be combined with one or more other same or similar systems and an entire system 140 may be made up of multiple computing devices communicating with each other.

FIG. 1 also illustrates an operator input system 140 and a resource input system 141, in accordance with an embodiment of the invention. Each system (the operator input system 140 and the resource input system 141) includes a processor 152, memory 154, an input/output device such as a display 156, a communication interface 158, and a transceiver 160, among other components. The user input system 140 may also be provided with a storage device, such as a microdrive or other device, to provide additional storage. Each of the components 152, 154, 158, and 160, are interconnected using various buses, and several of the components may be mounted on a common motherboard or in other manners as appropriate.

The processor 152 is configured to execute instructions within the user input system 140, including instructions stored in the memory 154. The processor may be implemented as a chipset of chips that include separate and multiple analog and digital processors. The processor may be configured to provide, for example, for coordination of the other components of the operator input system 140 and the resource input system 141, such as control of user interfaces, applications, and wireless communication.

The processor 152 may be configured to communicate with the operator(s) and/or healthcare resource(s) through control interface 164 and display interface 166 coupled to a display 156. The display 156 may be, for example, a TFT LCD (Thin-Film-Transistor Liquid Crystal Display) or an OLED (Organic Light Emitting Diode) display, or other appropriate display technology. The display interface 156 may comprise appropriate circuitry and configured for driving the display 156 to present graphical and other information to an operator. The control interface 164 may receive commands or selections from an operator or healthcare resource and convert them for submission to the processor 152. In addition, an external interface 168 may be provided in communication with processor 152, so as to enable near area communication of the operator input system 140 and the resource input system 141 with other devices and each other. External interface 168 may provide, for example, for wired communication in some implementations, or for wireless communication in other implementations, and multiple interfaces may also be used.

The memory 154 stores information within the operator input system 140 and the resource input system 141. The memory 154 can be implemented as one or more of a computer-readable medium or media, a volatile memory unit or units, or a non-volatile memory unit or units. Expansion memory may also be provided and connected to user input system 140 through an expansion interface (not shown), which may include, for example, a SIMM (Single In Line Memory Module) card interface. Such expansion memory may provide extra storage space, or may also store applications or other information therein. In some embodiments, expansion memory may include instructions to carry out or supplement the processes described above, and may include secure information also. For example, expansion memory may be provided as a security module for the operator input system 140 and the resource input system 141, and may be programmed with instructions that permit secure use of the systems. In addition, secure applications may be provided via the SIMM cards, along with additional information, such as placing identifying information on the SIMM card in a non-hackable manner. In some embodiments, the operator may interact with the applications to execute processes described with respect to the process flows described herein. Specifically, the application interacts with the process flow discussed in greater detail with respect to FIG. 2. It will be understood that the one or more applications stored in the system 130 and/or the operator input system 140 and the resource input system 141 may interact with one another and may be configured to implement any one or more portions of the various user interfaces and/or process flow described herein.

The memory 154 may include, for example, flash memory and/or NVRAM memory. In one aspect, a computer program product is tangibly embodied in an information carrier. The computer program product contains instructions that, when executed, perform one or more methods, such as those described herein. The information carrier is a computer- or machine-readable medium, such as the memory 154, expansion memory, memory on processor 152, or a propagated signal that may be received, for example, over transceiver 160 or external interface 168.

In some embodiments, the operator(s) may use the operator input system 140 to transmit and/or receive information or commands to and from the system 130. The healthcare resource(s) may use the resource input system 141 to transmit and/or receive information or commands to and from the system 130. In this regard, the system 130 may be configured to establish a communication link with the operator input system 140 and the resource input system 141, whereby the communication link establishes a data channel (wired or wireless) to facilitate the transfer of data. In doing so, the system 130 may be configured to access one or more aspects of the operator input system 140 and/or the resource input system 141, such as, a GPS device, an image capturing component (e.g., camera), a microphone, a speaker, or the like.

The operator input system 140 and the resource input system 141 may communicate with the system 130 (and one or more other devices) wirelessly through communication interface 158, which may include digital signal processing circuitry. Communication interface 158 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 160. In addition, short-range communication may occur, such as using a Bluetooth, Wi-Fi, or other such transceiver (not shown). In addition, GPS (Global Positioning System) receiver module 170 may provide additional navigation- and location-related wireless data to the operator input system 140 and/or the resource input system 141, which may be used as appropriate by applications running thereon, and in some embodiments, one or more applications operating on the system 130.

The operator input system 140 and/or the resource input system 141 may also communicate audibly using audio codec 162, which may receive spoken information from an operator or healthcare resource and convert it to usable digital information. Audio codec 162 may likewise generate audible sound for an operator or healthcare resource, such as through a speaker, e.g., in a handset of the operator input system 140 and/or the resource input system 141. Such sound may include sound from voice telephone calls, may include recorded sound (e.g., voice messages, music files, etc.) and may also include sound generated by one or more applications operating on the operator input system 140 and/or the resource input system 141, and in some embodiments, one or more applications operating on the system 130.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the operator and a keyboard and a pointing device (e.g., a mouse or a trackball) by which the operator can provide input to the computer. Other kinds of devices can be used to provide for interaction with an operator or healthcare resource as well; for example, feedback provided to the operator or healthcare resource can be any form of sensory feedback (e.g., visual feedback, auditory feedback, or tactile feedback); and input from the operator or healthcare resource can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

It will be understood that the embodiment of the system environment illustrated in FIG. 1 is exemplary and that other embodiments may vary. As another example, in some embodiments, the system 130 includes more, less, or different components. As another example, in some embodiments, some or all of the portions of the system environment 100 may be combined into a single portion. Likewise, in some embodiments, some or all of the portions of the system 130 may be separated into two or more distinct portions.

FIG. 2 is a high-level process flow diagram illustrating a process using the resource scheduling system 130, in accordance with one embodiment of the present disclosure. The process begins at block 202, where the system 130 establishes a communication channel with one or more data source(s). In some embodiments, the one or more data source(s) may be external data source(s), such as local or remote software applications, databases, computing devices, and/or the like. In some embodiments, the data source(s) may comprise a local memory of the system, operator input system, and/or resource input system. The system may be configured to maintain the communication channel with the one or more data source(s) over time and/or may be configured to re-establish the communication channel in response to receiving an input from the resource input system as is described in greater detail herein.

The process may then continue to block 204, where the system receives a data transmission from the one or more data source(s). In some embodiments, the one or more data source(s) may be external data sources such as practice management systems, electronic health record systems, payroll systems, and/or the like. The data transmission may comprise supply data, or data regarding scheduled availability of a type of healthcare resource. For example, in some embodiments, the data transmission may comprise data such as a personnel schedule or the like for one or more individuals. The data transmission may further comprise a plurality of healthcare resource datasets, where each healthcare resource dataset contains information associated with a particular healthcare resource (e.g., contact information, resource type, resource certifications, resource location(s), resource availability, and/or the like).

The process may then continue to block 206, where the system receives a second data transmission from one or more data source(s). In some embodiments, the one or more data source(s) may be external data sources such as practice management systems, electronic health record systems, payroll systems, and/or the like. The second data transmission may comprise demand data, or data associated with demand for a type of healthcare resource. For example, in some embodiments, the second data transmission may comprise data associated with scheduled appointments (e.g., appointment type, appointment time, appointment cancellation(s) or confirmation(s), resource requests associated with scheduled appointments, and/or the like). In some embodiments, the second data transmission may comprise data identifying a demand for particular resource types associated with the scheduled appointments. Additionally or alternatively, the system may be configured to determine, based on the second data transmission, the demand for particular resource types associated with the scheduled appointments. In some embodiments, the system may receive the data transmission and/or the second data transmission via a system integration with the one or more data source(s). Additionally or alternatively, the system may receive the data transmission and/or the second data transmission via a data packet exchange over a wireless communication channel.

The process may then continue to block 208, where the system calculates differential demand for the type of healthcare resource. In some embodiments, the system may calculate differential demand based on the data regarding scheduled availability and the data associated with demand. The system may apply one or more demand categories to each scheduled appointment from the second data transmission. For example, the system may categorize a scheduled appointment as both a "returning patient appointment" and as an "MRI appointment." In some embodiments, for each time period of a plurality of time periods, the system may calculate the difference between the demand for a particular resource type and the number of said resource types available during the time period. For example, the system may determine, based on the scheduled availability data, that four medical technicians are scheduled between 9 AM and 10 AM. The system may also determine, based on the demand data, that five medical technicians are required for the number of appointments occurring or expected to occur between 9 AM and 10 AM. The system may make this determination based on weighting of a resource type need associated with each demand category of the scheduled appointments. As such, the system may calculate a differential demand of one medical technician between 9 AM and 10 AM. The differential demand may be a net positive number associated with a supply surplus, may be a net negative number associated with unmet demand, or may be zero.

The system may then determine, via an optimization engine, at least one suggested resource assignment. The suggested resource assignment may be a suggestion to schedule an additional resource or a suggestion to remove a currently scheduled resource from a schedule. In some embodiments, the system may determine the at least one suggested resource assignment based on the differential demand for the type of healthcare resource. For example, the system may determine that a medical technician should be scheduled for an 8 AM to 12 PM shift, or should be removed from an 8 AM to 12 PM shift, in order to meet the differential demand. The features and functions of the optimization engine are discussed in greater detail with respect to FIG. 5.

The process may then continue to block 210 where the system causes an operator device to display a user interface. The user interface may display a visual representation of the differential demand for the type of healthcare resource and a visual representation of the suggested resource assignment. In some embodiments, the visual representation of the suggested resource assignment is selectable by an operator of the operator device. In some embodiments, the user interface may additionally display a current resource schedule. Continuing with the above example, the user interface may display a plurality of time periods, including a time period between 9 AM and 10 AM. The user interface may further display a visual indication representing the four medical technicians scheduled during said time period, as well as a visual indication representing the demand of one medical technician during said time period. Furthermore, the user interface may display a suggested resource assignment of one medical technician during the time period. The suggested resource assignment may be selectable to an operator of the system. The features and functions of the user interface are described in greater detail with respect to FIG. 6.

The process may then continue to block 212 wherein the system receives, from the operator device, an operator selection. The operator selection may comprise a selection of the suggested resource assignment in the user interface. In some embodiments, in response to the operator selection of the operator selection comprising the selection of the suggested resource assignment, the system may query the plurality of healthcare resource datasets to determine a list of available resources. For example, the system may query the plurality of healthcare resource datasets to identify resources of a particular type that are not otherwise scheduled during the time period. In addition, the system may query for characteristics such as preferred resource location, availability during other time periods, cost of the resource, and/or the like. The system may then use said characteristics to determine a list of available resources, where the available resources may be ranked based on a predetermined characteristic and/or an operator selection of a characteristic, such as resource proximity to the managing entity. Next, the system may cause the operator device to display, via the user interface, the selectable list of available resources of the type of healthcare resource. In some embodiments, the system may then receive a second operator selection. The second operator selection may comprise a selection of a particular available resource from the list of available resources.

The process may then continue to block 214, where the system transmits an assignment notification to a computing device associated with the particular available resource of the type of healthcare resource, or the selected available resource. In some embodiments, the assignment notification may comprise a message notifying the particular available resource that the resource has been scheduled for a particular time period. In some embodiments, the assignment notification may comprise a request to schedule the resource and may provide the particular available resource with an option to accept or deny the request. The system may then receive an acceptance from the computing device associated with the particular available resource and may update the user interface to reflect new availability and differential demand information. Additionally or alternatively, the system may receive a denial from the computing device associated with the particular available resource. In such embodiments, the system may then, in response to a third operator selection, transmit an assignment notification to a different resource from the list of available resources. The system may continue to transmit assignment notifications in response to operator inputs until an acceptance is received, at which point the system may update the user interface to reflect new availability and differential demand information.

FIG. 3 is a high-level process flow diagram illustrating a process 300 for determining differential demand per time slot using the resource scheduling system 130, in accordance with one embodiment of the present disclosure. The process may begin at block 302, where the system may identify or receive a plurality of time-based records. The time-based records may include availability data, such as resource shifts, and/or demand data, such as scheduled appointments. Next, the system may identify a plurality of time slots 304 over a predetermined period of time. For example, the system may identify a plurality of 15 minute intervals over the course of eight hours. In another example, the system may identify of plurality of one hour intervals over the course of twenty four hours. In some embodiments, the number of time slots and the predetermined period of time may be selectable via an operator of the user interface.

The process may then continue to block 306, where for each time slot and each time-based record, the system determines whether the time-based record occurs within the time slot. For example, a time-based record may be an hour-long appointment scheduled from 9:30 AM to 10:30 AM. The system may then determine that the appointment falls within a 9 AM to 10 AM time slot and a 10 AM to 11 AM time slot. The system may further determine that appointment does not fall within an 11 AM to 12 PM time slot, or any other time slots of the plurality of time slots. Next, as shown in block 308, the system may calculate a total count of time-based records occurring within each time slot, and may differentiate between availability records and appointment records. For example, the system may determine that in the time slot from 9 AM to 10 AM, there are four appointments occurring within that time slot and four resources scheduled during that time slot.

The process may conclude in block 310, where the system may use the outputs of block 308 to calculate a differential demand for each time slot. Continuing with the above example, the system may identify, based on the four appointments occurring in the 9 AM to 10 AM time slot, that four medical technicians, or other resource types, are required to meet the time slot demand. The system may then identify, based on the four resources scheduled during the time slot, that only two of the scheduled resources are of the correct type to meet the time slot demand. As such, the system may calculate a differential demand of two medical technicians during the 9 AM to 10 AM timeslot. In another example, the system may identify, based on six scheduled resources during the time slot, that all six of the scheduled resources are of the correct type to meet the time slot demand. As such, the system may calculate a positive differential demand, or surplus, of two medical technicians during the 9 AM to 10 AM timeslot.

FIG. 4 is a high-level process flow diagram illustrating a process 400 for adjusting the demand output of FIG. 3 using historical and predicted data patterns. The process 400 uses the resource scheduling system 130, in accordance with one embodiment of the present disclosure. The process may begin in block 402, where the system receives, from a data source, an expected demand for each time slot of a plurality of time slots. The data source may be an external data source and/or may be a local memory store associated with the system 130. In some embodiments, the system may receive a predicted demand for a period of time such as a day and may use the features and functions described in FIG. 3 to convert the total predicted demand to a predicted demand per time slot. The predicted demand may be based on historical demand data and may be calculated using predictive modeling. For example, if a particular resource typically manages four appointments in a day, the predicted demand may be four appointments for each day that the resource is scheduled. In some embodiments, the system may use predicted demand data instead of actual demand data and/or may adjust actual demand data based on predicted demand data. For example, if the predicted demand for a type of resource is four appointments on a date occurring in the next month, the system may use the predicted demand to determine a differential demand per time slot. However, if no appointments are scheduled over the course of the month, the system may replace the predicted demand data with the actual demand data (e.g., zero appointments) in order to calculate a differential demand per time slot.

Subsequently or simultaneously, the process flow may continue to block 404, where the system may receive, from a data source, a historical supply pattern associated with the expected or actual demand data. The data source may be the same data source associated with the expected demand data or may be a different data source. In some embodiments, the historical supply pattern may identify a historical resource time and/or resource type required for each appointment type and/or appointment location. For example, while an appointment may be scheduled from 9 AM to 10 AM, an associated historical supply pattern may indicate that similar appointments typically require a particular resource type, such as a nurse, from 8:45 AM until 9:30 AM and a second resource type, such as a doctor, from 9:30 AM until 10:15 AM. As such, the historical supply patterns may be used to dynamically adjust differential demand data by adjusting the types of resources required and the time slots that each resource is required for.

The process may then continue to block 406, where the system may calculate adjusted differential demand data based on the expected demand and/or the historical supply patterns. In some embodiments, the system may regularly receive updated expected demand and/or historical supply patterns and may regularly calculate adjust differential demand data every time updated data is received. For example, the system may receive updates daily or hourly, or may receive updates when an expected demand or historical supply pattern changes. In some embodiments, the system may take into account, when calculating differential demand data, how far into the future the differential demand is positioned. For example, when the system calculates differential demand data for a time period several months or weeks in advance, the system may rely primarily on expected demand data and historical supply patterns in making the calculation. When the system calculates differential demand data for a time period several days or hours in advance, it may rely primarily on actual demand data received from the one or more data source(s).

FIG. 5 is a high-level process flow diagram illustrating a process 500 for providing shift recommendations using the resource scheduling system 130, in accordance with one embodiment of the present disclosure. The system may begin at block 502, where the system may determine, based on an operator selection, a set of optimization parameters. Optimization parameters may comprise any resource scheduling parameters such as economic parameters (e.g., hourly cost per resource type, minimum and maximum scheduled hours per resource type, and/or the like), availability parameters (e.g., current resource schedule, minimum staffing level per resource type, fixed staffing level per resource type, and/or the like), and/or preferred shift parameters. Preferred shift parameters may provide the system with instructions to weight particular shifts based on operator preferences. For example, shifts with a duration closer to 8 hours may be more preferred than shorter or longer shifts. In another example, shifts with start times on an hour or half hour (e.g., 9 AM, 10:30 AM, etc.) may be more preferred than shifts with other start times (e.g., 7:10 AM, etc.).

Next, the process flow may continue to block 504, where the system may input differential demand data, resource availability data, and the optimization parameters into an optimization engine. The optimization engine may comprise any mathematical algorithms configured to produce an optimized solution or set of solutions based on a set of inputs and parameters. The differential demand data may be actual demand data and/or adjusted demand data as is discussed in greater detail with respect to FIGS. 3 and 4.

The process flow may then continue to block 506, where the system may determine, based on an output of the optimization engine, at least one solution set. The at least one solution set may comprise a suggested shift or set of suggested shifts designed to meet the differential demand per time slot, without deviating from the optimization parameters. In some embodiments, the system may be configured to determine a solution set for each resource type. For example, on a particular date, the system may determine that there is a need for two clinical resources working from 8 AM until 5 PM, one clinical resource working from 10 AM until 3 PM, and three non-clinical resources working from 7 AM until 2 PM. As differential demand is updated, the system may also update the optimization engine to determine an updated solution set.

The process may then continue to block 508, where the system may display, via the user interface, the at least one solution set. As is discussed in greater detail with respect to FIG. 2, the user interface may provide a selectable shift of the solution set such that an operator may select a shift and identify an available resource to fill said shift. In some embodiments, the user interface may also comprise a selectable icon allowing the operator to create a new shift other than a shift from the solution set. In such embodiments, the system may then determine a new suggested solution set in response to an operator manually creating a new shift via the user interface.

FIG. 6 illustrates the user interface for the resource scheduling system, in accordance with an embodiment of the present disclosure. The user interface 600 may include an icon indicating a date 601. In some embodiments, the date icon 601 may be a day, week, or month and may indicate a past, present, or future date. The user interface 600 may further include a current schedule 602, which may visually indicate the resource availability data, or current supply data. For example, the current schedule 602 may comprise a list of healthcare resources 622, as well as a plurality of scheduled shifts 612 associated with each healthcare resource 622. As illustrated, each of the plurality of scheduled shifts 612 may display a time period associated with the scheduled shift and/or an expected resource demand during the scheduled shift. As is discussed in greater detail with respect to FIG. 4, the expected resource demand may reflect a predicted demand, an actual demand, and/or a combination of predicted demand and actual demand.

The user interface 600 may further include an optimized schedule 603. The optimized schedule may visually reflect the outputs of the optimization engine as is discussed in greater detail with respect to FIG. 5. For example, the optimized schedule 603 may display a plurality of suggested resource assignments 613, where each suggested resource assignment indicates a shift time period, as well as a number of resources required for the shift. Each suggested resource assignment 613 may include a selectable "add" icon 604, which may allow an operator to query the system for a list 630 of available resources to fill the suggested shift 613. In some embodiments, where the differential demand associated with the suggested resource assignment is positive, indicating a resource surplus, a suggested resource assignment 613 may include a selectable "remove" icon 604, which may allow an operator to remove a scheduled resource assignment from the resource availability data. The list 630 of available resources may include information identifying resources that meet the requirements to fill the shift, such a resource type and/or location. The list 630 may further include a selectable "add shift" icon 631 associated with each resource such that when selected, a message is transmitted to a user device associated with the resource. In some embodiments, the user interface 600 may further include a selectable "add shift" icon 614, which may allow an operator to query the system for a list of available resources for any time period, regardless of whether the time period is associated with a suggested resource assignment 613.

The user interface may further indicate a plurality of time slots 615, which may correspond to the plurality of time slots discussed in greater detail with respect to FIG. 3. In some embodiments, the time slots 615 may be hour-long increments, half-hour increments, fifteen minute increments, and/or the like. Each time slot 615 may be associated with a differential demand indicator 605, which may display the adjusted differential demand for each time slot as determined by the process flow of FIG. 4. In some embodiments, each time slot 615 may be associated with multiple differential demand indicators 605, such as differential demand by resource type (e.g., differential demand for clinical staff, differential demand for non-clinical staff, and/or the like).

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EEPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F #.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system providing an improved electronic interface for healthcare resource scheduling, the system comprising:
   non-volatile memory and volatile memory; and
   at least one processing device coupled to the non-volatile memory and volatile memory, wherein the at least one processing device utilizes the volatile memory by storing multiple pieces of information in the volatile memory to thereby reduce load on the system and increase processing speed, wherein the at least one processing device is further configured to:
      cause an operator device to display a user interface that comprises:
         a plurality of time periods associated with a particular date;
         a visual representation of a differential demand for a type of healthcare employee or contractor for the plurality of time periods;
         a suggested shift, the suggested shift comprising a shift length and a first selectable icon; and
         one or more shifts associated with the plurality of time periods, wherein the one or more shifts represent a personnel schedule;
      receive one or more data transmissions from an external data source, wherein the one or more data transmissions comprise data regarding shift information of the type of healthcare employee or contractor and data associated with a demand for the type of healthcare employee or contractor, wherein the shift information comprises at least one resource scheduling parameter;
      based on the data regarding shift information of the type of healthcare employee or contractor and the data associated with the demand for the type of healthcare employee or contractor, update differential demand for the type of healthcare employee or contractor in the user interface;

based on the differential demand for the type of healthcare employee or contractor, update the suggested shift, wherein the shift length of the suggested shift is based on the at least one resource scheduling parameter;

receive, via the user interface, an operator selection of the first selectable icon;

in response to the operator selection, display, via the user interface, a menu comprising a list of available employees or contractors of the type of healthcare employee or contractor, wherein each entry of the list comprises a second selectable icon;

in response to receiving a second operator selection comprising a selection of the second selectable icon of one entry of the list, initiate electronic communication with a user device; and update the one or more shifts in the user interface based on the electronic communication with the user device.

2. The system of claim 1, wherein the data regarding shift information of the type of healthcare employee or contractor comprises information identifying an employee or contractor, employee or contractor type, and employee or contractor location, and wherein the data regarding shift information is compiled from a plurality of external data sources.

3. The system of claim 1, wherein the menu comprises a pop-up window and wherein the list of available employees or contractors is sorted according to at least one predetermined characteristic.

4. The system of claim 1, wherein the first selectable icon displays a category of personnel utilized by a healthcare provider.

5. The system of claim 1, wherein updating differential demand for the type of healthcare employee or contractor further comprises calculating, for each time period of the plurality of time periods, a demand for the type of healthcare employee or contractor.

6. The system of claim 5, wherein the visual representation of the differential demand for the type of healthcare employee or contractor for the plurality of time periods visually indicates whether the differential demand is a positive value or a negative value.

7. The system of claim 1, wherein the differential demand is updated at least in part based on historical availability data for the type of healthcare employee or contractor.

8. The system of claim 1, wherein the differential demand is updated at least in part based on historical demand data for the type of healthcare employee or contractor.

9. The system of claim 1, wherein the shift length is updated based on an optimization algorithm, at least one predetermined parameter, and at least one preferred parameter wherein the preferred parameter is based on a third operator selection via the user interface.

10. The system of claim 1, wherein the at least one processing device is further configured to receive an assignment acceptance from the user device.

11. The system of claim 1, wherein the at least one processing device is further configured to:

receive an assignment denial from the user device; and initiate electronic communication with a second user device based on a third operator selection via the user interface.

12. A computer-implemented method of providing an improved electronic interface for autonomous resource scheduling, wherein the computer-implemented method is performed using a system that comprises non-volatile memory, volatile memory, and at least one processing device coupled to the non-volatile memory and volatile memory, the computer-implemented method comprising:

causing an operator device to display a user interface that comprises:

a plurality of time periods associated with a particular date;

a visual representation of a differential demand for a type of healthcare employee or contractor for the plurality of time periods;

a suggested shift, the suggested shift comprising a shift length and a first selectable icon; and one or more shifts associated with the plurality of time periods, wherein the one or more shifts represent a personnel schedule;

receiving one or more data transmissions from an external data source, wherein the one or more data transmissions comprise data regarding shift information of the type of healthcare employee or contractor and data associated with a demand for the type of healthcare employee or contractor, wherein the shift information comprises at least one resource scheduling parameter;

based on the data regarding shift information of the type of healthcare employee or contractor and the data associated with the demand for the type of healthcare employee or contractor, updating the differential demand for the type of healthcare employee or contractor in the user interface;

based on the differential demand for the type of healthcare employee or contractor and an output determined by an optimization engine, updating the suggested shift, wherein the shift length of the suggested shift is based on the at least one resource scheduling parameter;

receiving, via the user interface, an operator selection of the first selectable icon;

in response to the operator selection, displaying, via the user interface, a menu comprising a list of available employees or contractors of the type of healthcare employee or contractor, wherein each entry of the list comprises a second selectable icon;

in response to receiving a second operator selection comprising a selection of the second selectable icon of one entry of the list, initiating electronic communication with a user device associated with a particular available employee or contractor and transmitting an assignment notification to the user device, wherein the assignment notification comprises at least one user-selectable option; and updating the one or more shifts in the user interface based on the electronic communication with the user device;

wherein the system utilizes the volatile memory by storing multiple pieces of information in the volatile memory to thereby reduce load on the system and increase processing speed.

13. The computer-implemented method of claim 12, wherein the data regarding shift information of the type of healthcare employee or contractor comprises information identifying an employee or contractor, employee or contractor type, and employee or contractor location, and wherein the data regarding shift information is compiled from a plurality of external data sources.

14. The computer-implemented method of claim 12, wherein the menu comprises a pop-up window and wherein the list of available employees or contractors is sorted according to at least one predetermined characteristic.

15. The computer-implemented method of claim 12, wherein the visual representation of the differential demand for the type of healthcare employee or contractor for the plurality of time periods visually indicates whether the differential demand is a positive value or a negative value.

16. The computer-implemented method of claim 12, further comprising:
    receiving an assignment denial from the user device; and
    initiating electronic communication with a second user device based on a third operator selection via the user interface.

17. A computer-implemented method of providing an improved electronic interface for healthcare resource scheduling, wherein the computer-implemented method is performed using a system that comprises non-volatile memory, volatile memory, and at least one processing device coupled to the non-volatile memory and volatile memory, the computer-implemented method comprising:
    generating a user interface for display on an operator device, wherein the user interface comprises:
        a first portion configured to present a plurality of time periods associated with a particular date, wherein the first portion comprises a visual representation of a differential demand for a type of healthcare employee or contractor for each of the plurality of time periods,
        a second portion configured to present a suggested shift, wherein the suggested shift comprises a first selectable icon and a shift length,
        a third portion configured to present a ranked list of available resources of the type of healthcare employee or contractor, wherein at least one entry of the ranked list is associated with a second selectable icon and wherein the third portion is presented in response to a first operator selection of the first selectable icon, and
        a fourth portion configured to present one or more shifts associated with the plurality of time periods, wherein the one or more shifts represent a personnel schedule;
    updating the first portion of the user interface based on a first computing process, wherein the first computing process comprises calculating the differential demand for the type of healthcare employee or contractor for each of the plurality of time periods;
    electronically receiving shift information from an external data source, wherein the shift information comprises at least one resource scheduling parameter;
    updating the second portion of the user interface based on a second computing process, wherein the second computing process comprises generating, via an optimization engine, the suggested shift, wherein the shift length of the suggested shift is based on the at least one resource scheduling parameter and wherein the optimization engine is configured to receive a set of optimization parameters;
    updating the third portion of the user interface based on a third computing process, wherein the third computing process comprises generating the ranked list associated with the suggested shift;
    presenting the third portion in response to the first operator selection of the first selectable icon;
    in response to a second operator selection of the second selectable icon of one entry of the ranked list, initiating electronic communication with a user device; and
    updating the fourth portion based on the electronic communication with the user device;
    wherein the system utilizes the volatile memory by storing multiple pieces of information in the volatile memory to thereby reduce load on the system and increase processing speed.

18. The computer-implemented method of claim 17, wherein the ranked list of available resources is sorted according to at least one predetermined characteristic.

19. The computer-implemented method of claim 17, wherein the visual representation of the differential demand visually indicates whether the differential demand is a positive value or a negative value.

20. The computer-implemented method of claim 17, further comprising:
    receiving an assignment denial from the user device; and
    initiating electronic communication with a second user device based on a third operator selection via the user interface.

* * * * *